United States Patent [19]

Henrichsen et al.

[11] 4,430,062
[45] Feb. 7, 1984

[54] DENTAL APPARATUS WITH A NUMBER OF DENTAL INSTRUMENTS CONNECTED TO A COMMON CONTROL CIRCUIT AND A COMMON OPERATOR UNIT

[75] Inventors: Frank Henrichsen, Dragor; Flemming Hansen, Ballerup; Kim Sorensen, Lyngby, all of Denmark

[73] Assignee: A/S Flex Dental, Glostrup, Denmark

[21] Appl. No.: 272,061

[22] Filed: Jun. 9, 1981

[30] Foreign Application Priority Data

Jun. 13, 1980 [DK] Denmark .................. 2551/80

[51] Int. Cl.³ .......................................... A61C 1/02
[52] U.S. Cl. ........................................ 433/28; 433/101
[58] Field of Search ............... 433/27, 28, 98, 100, 433/101

[56] References Cited

U.S. PATENT DOCUMENTS

| | | |
|---|---|---|
| 3,081,542 | 3/1963 | Sherfey .................. 433/101 |
| 3,259,430 | 7/1966 | Beach .................... 433/101 |
| 3,778,903 | 12/1973 | Gardella et al. ........... 433/28 |
| 3,872,593 | 3/1975 | Thornton, Jr. et al. ...... 433/28 |
| 4,180,812 | 12/1979 | Kaltenbach et al. ........ 433/101 |
| 4,363,626 | 12/1982 | Schmidt et al. ........... 433/100 |

FOREIGN PATENT DOCUMENTS

| | | |
|---|---|---|
| 1466974 | 7/1970 | Fed. Rep. of Germany ...... 433/101 |
| 2434094 | 1/1976 | Fed. Rep. of Germany ...... 433/28 |
| 2530158 | 1/1977 | Fed. Rep. of Germany ...... 433/101 |
| 2339827 | 2/1977 | Fed. Rep. of Germany ...... 433/101 |
| 2604246 | 8/1977 | Fed. Rep. of Germany ...... 433/28 |

Primary Examiner—John J. Wilson
Attorney, Agent, or Firm—Schwartz, Jeffery, Schwaab, Mack, Blumenthal & Koch

[57] ABSTRACT

In a dental apparatus, in which each of a number of instruments is controlled by a control circuit common to the instruments, which are connected with a common operator unit having a control member which is movable in planar directions out of a home position, auxiliary functions not related to the instrument operation may be carried out by means of the common operator unit by switching the apparatus to a second mode of operation, when all the instruments assume respective resting positions in an instrument carrier. Moreover, also auxiliary functions directly related to the instrument operation may be carried out by the common operator unit in a first mode of operation by actuating the control member thereof with a movement different from the instrument energizing movement. The movement for energizing such an auxiliary function may have another direction and/or a shorter duration than the instrument energizing movement. In addition, the apparatus may be constructed to energize an air blow automatically after each operation of a drilling instrument when the control member of the common operator unit returns to the home position in the first mode of operation.

9 Claims, 4 Drawing Figures

DENTAL APPARATUS WITH A NUMBER OF DENTAL INSTRUMENTS CONNECTED TO A COMMON CONTROL CIRCUIT AND A COMMON OPERATOR UNIT

The present invention relates to a dental apparatus of the kind, in which each of a number of instruments is controlled from a control circuit which is common to the instrument and is connected with a common operator unit such as a foot contact having a movable control member.

With a view to simplification in respect of labor and increase of safety in the operation of the dental instruments in such an apparatus, efforts have been made in recent years towards an increased extent of automatization of the operation functions related to the use of the instrument, so that the dentist is liberated to a great extent from separate hand or foot operation of individual control members for the instruments.

It is the object of the invention to provide a dental apparatus offering further simplification in respect of labor and improved safety in the performance of an increased number of operation functions in connection with the dentist's work.

According to a first aspect of the invention, a dental apparatus is provided, comprising a number of dental instruments arranged removably in individual positions in the carrier, instrument removal signal generators individually associated with each of the instrument positions, a control circuit common to the dental instruments, an instrument selector device incorporated in the control circuit and connected to the removal signal generators an instrument energizing and control device in the control circuit for energizing and controlling only one instrument at a time when selected by the selector device, an operator unit common to the instruments for controlling the energization and control of the selected instrument by the energizing and control means, the operator unit comprising a control member which is movable out of a home position to perform an instrument energizing movement, means in the control circuit for sensing the instrument energizing movement and actuating said energizing and control means in response thereto, selectively actuable function energizing devices for actuating auxiliary functions during a dental treatment, which are not related to the operation of the dental instruments; at least one such functioning energizing device being incorporated in the common control circuit, a mode switching device incorporated in the common control circuit and controlled by the instrument selector device for switching the dental apparatus between first and second modes of operation in response to at least one instrument being removed from its position or all instruments assuming their respective positions in the instrument carrier, respectively, first and second input control units incorporated in the common control circuit and being connected to the operator unit by the mode switching device in the first and second mode respectively, the first input control unit being connected with the instrument energizing and control means and the second input control unit being connected with the at least one function energizing device for energizing the auxiliary function governed by the device in response to movement of the control member of the operator unit in the second mode of operation.

The invention is primarily based on the recognition of the fact that the dentist's treatment of a patient in addition to the control functions directly related to the operation of the dental instrument involves a number of further auxiliary functions which are not directly related to the instrument operation and have hitherto been actuated by manual operation of separate member for each of the functions.

As examples of auxiliary functions not related to the instrument operation which in the apparatus according to the invention may advantageously be activated by means of the common operator unit in the second mode of operation in which all the dental instruments assume their respective positions in the instrument carrier, mention could be made of filling of water in the patient's rinsing glass, activation of a fountain flush for the spittle from the patient, generation of a call signal for the dentist's assistant and adjustment of the patient's chair by height control or change of the relative positions of seat, back and leg supports.

An increase of the number of auxiliary functions not related to the instrument operation which in the second mode of operation can be incorporated in the control circuit and the common operator unit may be attained in that the control member of the operator unit is disposed for planar movement in opposite directions out of said home position for instrument operation and is further movable in said home position in at least one direction perpendicular to the planar movement, the mode switching device being constructed to supply a number of different energizing signals to the second input control unit in the second mode of operation corresponding to the number of directions of movement of the control member out of the home position, a number of function energizing devices corresponding to the number of different energizing signals being connected to the second input unit for actuating individual different ones of the auxiliary functions in response to individual different ones of the energizing signals.

According to a second aspect of the invention, a dental apparatus is provided comprising an instrument carrier with a number of dental instruments arranged removably in individual positions in the carrier, instrument removal signal generators individually associated with each of the instrument positions, a control circuit common to the dental instruments, an instrument selector device incorporated in the control circuit and connected to the removal signal generators, an instrument energizing and control device in the control circuit for energizing and controlling only one instrument at a time when selected by the selector device, an operator unit common to the instruments for controlling the energization and control of the selected instrument by the energizing and control means, the operator unit comprising a control member which is movable out of a home position to perform an instrument energizing movement, means in the control circuit for sensing the instrument energizing movement and actuating the energizing and control means in response thereto, selectively acutable function energizing devices for actuating auxiliary functions related to the operation of the dental instruments, at least one such function energizing device being incorporated in the control circuit, an input control unit incorporated in the control circuit and connected with the instrument energizing and control means as well as said operator unit to sense the instrument energizing movement as well as a movement of the control member different from the instrument energizing movement, the at least one function energizing device being connected to the input control unit to be actuated therefrom in response to the different movement of the control member.

In this second aspect, the invention is primarily based on the recognition of the fact that the dentist's treatment of a patient in addition to the control functions directly related to the operation of the dental instrument involved a number of further auxiliary functions which are directly related to the instrument operation and have hitherto been actuated by manual operation of separate numbers for each of the functions.

As examples of auxiliary functions related to the instrument operation which by means of the apparatus according to the invention may advantageously be energized by a movement of the control member of the common operator unit different from the instrument energizing movement, mention could be made of control of the composition of water and air in a coolant which by use, for example, of a drilling instrument is sprayed by means of a spraying device provided directly on the instrument or the generation of an air blow for drying a cavity produced with a drilling instrument.

In an embodiment of the apparatus according to the second aspect of the invention, the movement of the control member of the operator unit different from the instrument energizing movement may be realized in that the control member of the operator unit is disposed for planar movement in opposite directions out of the home position for instrument operation and is further movable in the home position in at least one direction perpendicular to the planar movement, the operator unit being constructed to transmit a number of different energizing signals to the input control unit corresponding to the number of movement directions of the control member out of the home position, the input control unit being constructed to actuate the function energizing device in response to the energizing signal transmitted by the operator unit in response to the perpendicular movement of the control member. This embodiment is particularly suitable for a function energizing device in the form of a coolant control device.

As another possibility, the movement of the control member different from the instrument energizing movement may be realized in that a timing device is connected to the input control unit for measuring the duration of the planar instrument energizing movement of the control member, the input control unit being constructed to actuate the instrument energizing and control means only in response to a duration of the movement exceeding a prescribed minimum duration and to actuate the function energizing device in response to a shorter duration of the movement of the control member. This embodiment is particularly suitable for a function energizing device in the form of an air blow energizing device.

In a preferred embodiment of this second aspect of the invention, a dental apparatus is provided, comprising an instrument carrier with a number of dental instruments arranged removably in individual positions in the carrier, instrument removal signal generator individually associated with each of the instrument positions, a control circuit common to the dental instruments, an instrument selector device incorporated in the control circuit and connected to the removal signal generator, an instrument energizing and control device in the control circuit for energizing and controlling only one instrument at a time when selected by the selector device, an operator unit common to the instruments for controlling the energization and control of the selected instrument by the energizing and control means, the operator unit comprising a control member which is movable out of a home position to perform an instrument energizing movement, means in the control circuit for sensing the instrument energizing movement and actuating the energizing and control means in response thereto, selectively actuable first and second function energizing devices for actuating a first and a second auxiliary function related to the operation of the dental instruments being incorporated in the control circuit, an input control unit incorporated in the control circuit and connected with the instrument energizing and control means and the first and second function energizing devices as well as the operator unit, the control member of the operator unit being disposed for planar movement in opposite directions out of the home position for operation of the dental instruments and being further movable in the home position in at least one direction perpendicular to the planar movement, the operator unit being constructed to transmit a number of different energizing signals to the input control unit corresponding to the number of movement directions of the control member out of the home position, a timing device being connected to the input control unit for measuring the duration of the planar movement of the control member, the input control unit being constructed to actuate the first function energizing device in response to the energizing signal transmitted by the operator unit by the perpendicular movement of the control movement and to actuate the instrument energizing and control means and the second function energizing device in response to a duration of the planar movement of the control member exceeding or being shorter, respectively, than a prescribed minimum duration.

In this combination it may be advantageous in connection with a function energizing device in form, for example, of a coolant control device that the timing device is constructed to measure the duration of the energizing signal also for the perpendicular movement of the control member, the first function energizing device being constructed for cyclic adjustment of its respective auxiliary function through a number of control steps, the input unit being constructed to actuate the first function energizing device for a single step adjustment in response to a duration of the movement of the control member shorter than the prescribed minimum duration and through a number of steps in response to a longer duration of the movement of the control member.

According to a third aspect of the invention a dental apparatus is provided comprising at least one drilling instrument and an operator unit with a control member which is movable against spring action out of home position for energizing and controlling the drilling instrument, an instrument energizing device connected between the drilling instrument and the operator unit, a water spraying device and an air blowing device provided on the drilling instrument, water and air supplies connected with the water spraying and air blowing devices, valve devices arranged between the water and air supplies and the water spraying and air blowing device, and water spray and air blow energizing devices connected to the valve devices and the said instrument energizing device for producing a coolant spray during operation of the instrument, a selectively actuatable air blow energizing device with an associated valve device being provided at least for the air blowing device, the selectively actuatable air blow energizing device being connected to the operator unit for automatically supplying an opening signal to its associated valve device in response to the control member of the operator unit returning to the home position following a movement out of the position.

In a preferred embodiment of this third aspect of the invention the dental apparatus is constructed so that a timing device is connected between the selectively actuatable air blow energizing device and the operator unit for measuring the duration of the movement of the control member out of the home position and the selectively actuatable air blow energizing device is constructed to produce first or second opening signals for the associated valve device in response to the duration of the movement of the control member being shorter or longer, respectively, than a prescribed minimum duration.

In connection with this embodiment, if the control circuit is constructed so that energizing of the drilling instrument is only taking place, when the duration of the movement of the control member out of the home position exceeds the prescribed minimum duration, the drilling instrument may serve at a shorter duration of the movement of the control member as a separate air blowing device to produce an air blow, for example, in advance of a drilling operation.

In order to obtain a more efficient drying after a drilling operation, for example, with accompanying coolant spray, the timing device is preferably constructed so that the first opening signal comprises a single opening pulse, whereas the second opening signal comprises at least two succeeding opening pulses of different duration.

In the following, the invention will be explained in further detail with reference to the schematical drawings, wherein FIG. 1 is a simplified perspective view of a dentist's stand including a dental apparatus according to the invention;

Figure 1:
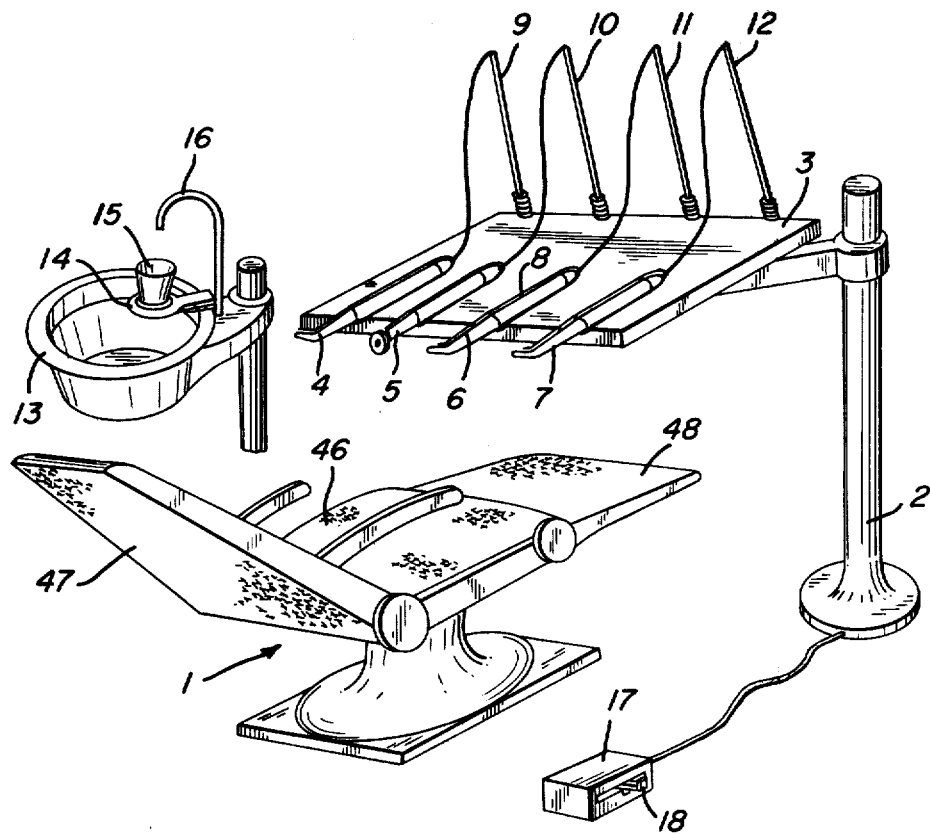

The dentist's stand shown in FIG. 1 comprises a patient's chair designated as a whole by 1. A stationary support 2, which is only schematically illustrated, is connected with an instrument carrier 3 having a number of separate positions for dental instruments 4 to 7. In a manner known per se, these instruments may comprise, for example, drilling instruments driven either by a motor having two directions of revolution and a continuously variable rotational speed, or by an air turbine which may have a fixed direction of revolution and rotational speed. As shown for the instrument 6, such drilling instruments may be provided with a device 8 for spraying a coolant composed of water and air during operation and for providing a pure air blow for drying a cavity made by means of the drilling instrument. The energy supply to the instruments 4 to 7 takes place through electric cables or air hoses which in the embodiment are carried over spring-biased pivot arms 9 to 12, for each of which a microcontact is provided in a manner, not illustrated, for generating a removal signal when the relevant instrument is lifted off from its position in the instrument carrier.

Finally, the treatment stand comprises a rinsing assembly with a fountain 13, a support 14 for a rinsing glass 15 and a water filling device 16.

For performing all control functions directly related to the operation of the instruments 4 to 7, as well as a number of further auxiliary functions not directly related to the instrument operation, the treatment stand further comprises a single common operator 17 which in the embodiment shown takes the form of a foot contact. The foot contact 17 has a control member 18 in the form of a projecting arm which may perform a planar horizontal movement to both sides out of a central home position, on one hand, and may perform, on the other hand, a movement perpendicular thereto when assuming the central position, such as a vertical downwards movement.

Figure 2:
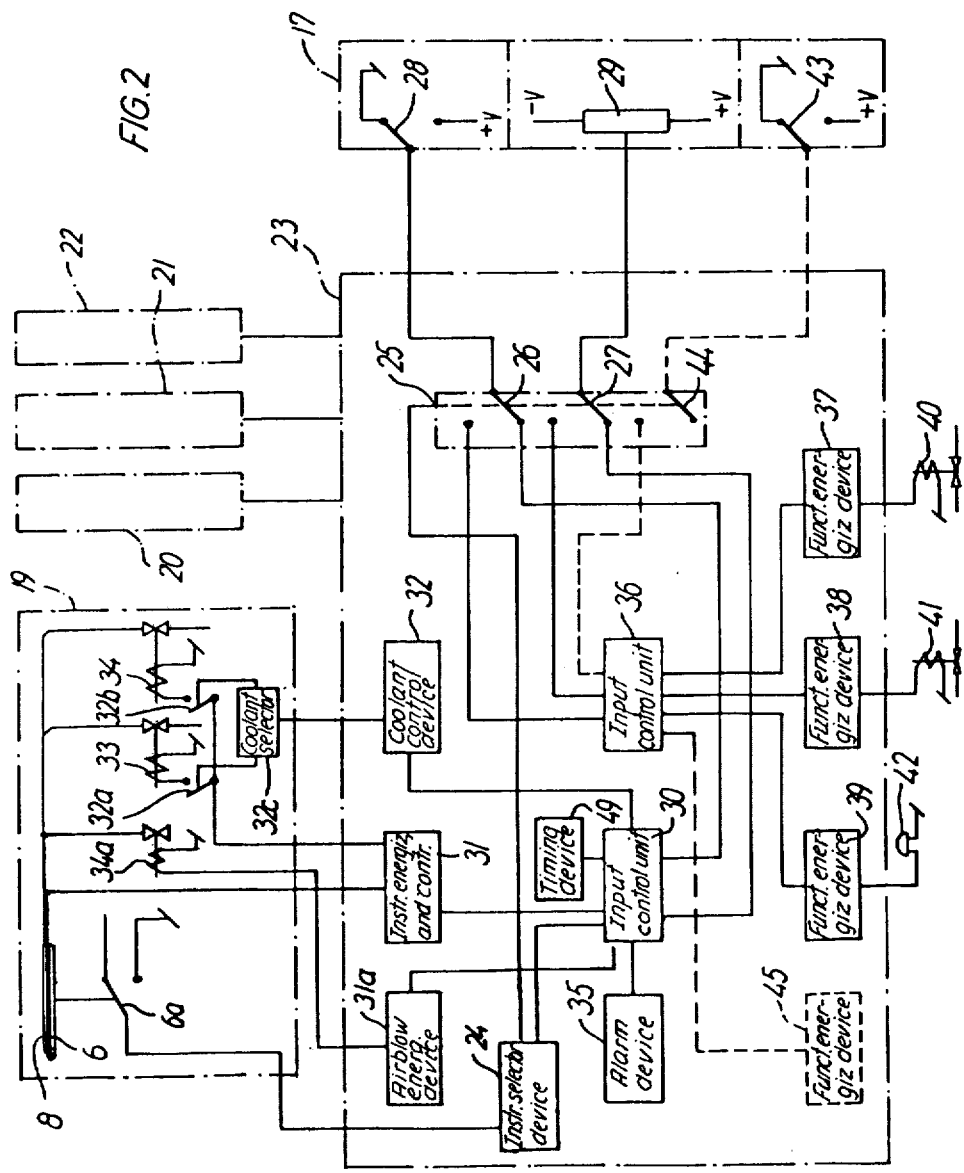
FIG. 2 is a simplified schematical diagram of an embodiment of the dental apparatus.

The schematic diagram in FIG. 2 illustrates the principal structure of the signal processing and actuating circuits of the dental apparatus. The instruments in the instrument carrier 3 are shown schematically by instrument blocks 19 to 22, the construction of which is only illustrated for the instrument block 19 associated with the instrument 6, since the remaining instrument blocks 20 to 22 are constructed, in principle, in a similar manner. The instrument blocks 19 to 22 are connected to a common control circuit 23, to which also the common operator unit 17 is connected.

The microcontact 6a associated with the pivot arm 11 for the instrument 6 is connected in the control circuit 23 to an instrument selector device 24, to which the corresponding microcontacts for the remaining instruments are also connected. The instrument selector device 24 may be constructed in such a way that only one of the instruments 4 to 7 may be actuated at a time, i.e. by actuation of any instrument, a blocking is established against actuation of the other instruments independent of their possible removal from the instrument carrier 3. Thereby, it is possible, for example, for the dentist's assistant to prepare another instrument for subsequent use independent of the dentist's use of an instrument.

Thus, since it will be recorded in the instrument selector device 24 at any time, whether one or more of the instruments 4 to 7 are lifted off, or all instruments assume their respective positions in the instrument carrier 3, the instrument selector device 24 is connected, in accordance with the invention, with a mode switching device 25 for switching the dental apparatus between a first mode of operation, in which at least one of the instruments 4 to 7 is lifted off, and a second mode of operation, in which all instruments assume their respective positions in the instrument carrier. In FIG. 2, the mode switching device 25 is illustrated purely schematically by two-position switches 26 and 27. In a similar manner, the construction of the operator unit 17 is illustrated purely schematically with a contact 28 which is actuated by the vertical downwards movement of the control member 18 and is connected to the switch 26 in the mode switching device 25 together with a voltage divider 29, the displaceable tapping of which is connected to the switch 27 in the mode switch device 25 and assumes a position corresponding to the position of the control member 18 in the horizontal movement.

In the first mode of operation, in which at least one of the instruments 4 to 7 is lifted off, the switches 26 and 27 are connected to a first input control unit 30, by means of which the operator unit 17 is connected for actuation of instrument energizing and control means 31 for an instrument selected for energization by the instrument selector device 24. For use in connection with instruments which like the instrument 6 shown in the figure are provided with a device 8 for spraying a coolant during operation, and for air blowing, magnet valves 33 and 34 actuating the supply of water and air in the coolant are connected to the energizing and control means 31, on one hand, and, on the other hand, a coolant control device 32 acting on contacts 32a and 32b in the instrument block for releasing or blocking each of the magnet valves 33 and 34, as well as an air blow energizing device 31a acting on a magnet 34a to produce the above mentioned air blow are connected to the input control unit 30.

When a drilling instrument driven by an electric motor and having two possible directions of revolution and a continuously variable rotational speed is energized by horisontal movement of the control member 18 out of the central position, the value of the voltage signal supplied from the voltage divider 29 through the switch 27 to the input control unit 30 corresponding to the movement of the control member 18 out of the home position serves for controlling the rotational speed of the selected drilling instrument via the energizing and control means 31. This speed control may advantageously be non-linear, so that on the major part of the movement of the control member 18 out of the central position, a relatively slow speed increase takes place and a strong increase towards full speed is not accomplished until near the extreme position. The sign of the voltage signal corresponding to the direction of the planar horizontal movement of the control member 18 out of the central position actuates the energizing and control means 31 to energize the drilling instrument in one direction of revolution or the other. Since in most normally occurring treatments dental drilling instruments must rotate clockwise, and counter-clockwise rotation is only prescribed for certain special treatments, an alarm device 35 may, furthermore, be connected to the input control unit 30 for supplying, for example, an acoustic alarm signal when the control member 18 has been moved to the side corresponding to counter-clockwise rotation of the drilling instrument, for example to the left.

If the instrument selected by means of the instrument selector device 24 is an air turbine powered drilling instrument, the control by means of the control member 18 may be an on-off control by which the instrument is energized with the prescribed direction of revolution and rotational speed independent of the direction of movement of the control member 18.

If a coolant spraying device is associated with a drilling instrument selected by means of the instrument selector device 24, said spraying device is actuated simultaneously with the energization of the instrument from the energizing and control means 31.

In the case of all the instruments 4 to 7 assuming their respective positions in the instrument carrier 3, the mode switching device 25 is switched by means of the instrument selector device 24 to the other position of each of the switches 26 and 27, the operator unit 17 is connected to a second input control unit 36, to which function energizing devices 37, 38 and 39 for energizing auxiliary functions not related to the instrument operation are connected.

As examples of such auxiliary functions, mention could be made of activation of a flushing device associated with the fountain 13 shown in FIG. 1 by means of a magnet valve 40 energized by the function energizing device 37, activation of the water filling device 16 shown in FIG. 1 by means of a magnet valve 41 energized by the function energizing device 38 and generation of a call signal for the dentist's assistant by remote energization of an acoustic signal generator 42, for example, by means of the function energizing device 39.

The above mentioned auxiliary functions are activated by the three above mentioned control movements of the control member 18 of the operator unit 17, i.e. the two oppositely directed horizontal movements out of the central position and the vertical downwards movement in the central position. The actuation may take place, for example, in such a manner that horizontal movement in one direction results in a time limited energization of the magnet valve 40, whereas horizontal movement in the other direction results in a time-limited energization of short duration of the magnet valve 41 followed by time-limited energization of the magnet valve 40, and vertical downwards movement results in energization of the signal generator 42.

In FIG. 2 a further possible movement of the control member 18 of the operator unit 17 in addition to the two oppositely directed horizontal movements and the vertical downwards movement is illustrated in dashed lines, namely a horizontal inwards movement of the control member 18 in its central position perpendicular to the above mentioned movements. Thereby, a contact 43 is closed, which is connected through a switch 44 in the mode switching device 25 to the input control unit 36 in the second mode of operation and causes the input control unit 36 to actuate a function energizing device 45 for energizing a fourth auxiliary function. As an example of such a function, adjustment of the patient's chair 1 in FIG. 1 could be mentioned. The patient's chair 1 comprises a seat 46 which is adjustably connected with a back 47 and a leg support 48, adjusting means for height control and control of the relative positions of seat and back being associated with the patient's chair. It is known in the art to design these adjusting means in such a way that the chair is usually moved between two fixed adjustments, viz. a treatment position with the back laid down to a lying position of the patient and a raised position for use when the patient enters or leaves the chair or uses the rinsing glass 15 and the fountain 13. By means of the additional movement possibility for the control member 18 and the actuation of the control circuit 23 associated therewith, a simple switching between the two positions without operation of separate operating members is obtained.

In addition to the described switching of the apparatus between first and second modes of operation and the possibility resulting therefrom for actuating a number of auxiliary functions not related to the instrument operation, use is made in the embodiment shown of a wide-going automization of the instrument operation per se by allowing also auxiliary functions like coolant control and actuation of an air blow to be performed by means of the common control circuit 23 and the common operator unit 17 connected therewith. For this purpose, a timing device 49 may be connected to the input control unit 30 to measure in the first mode of operation the duration of a voltage signal from the voltage divider 29 through the switch 27 generated by horizontal movement of the control member 18 as well as a signal from the contact 28 through the switch 26 generated by vertical downwards movement of the control member 18.

However, the input control unit 30 may also be constructed so that said air-blow is only energized by movement of the control 18 to one side, for example to the right, whereas a short movement of the control member 18 to the other side energizes a flashing spray comprising water as well as air in a predetermined mixing ratio.

The coolant control device 32 is constructed for stepwise control of the combination of water and air, respectively, in the coolant by means of the contacts 32a and 32b, for example, in four control steps corresponding to neither water nor air (no coolant), water alone, air alone, or both water and air in a predetermined cyclic order of succession of the control steps. The input control unit 30 co-operates with the timing device 49 in such a manner that by actuating of the contact 28 with a duration shorter than the predetermined minimum time, the coolant control device 32 will be actuated to a single step change of the water-air combination, whereas in case of a prolonged actuation of the contact 28, the coolant control device 32 will be actuated to go cyclically through the control steps during the actuation of the contact 28. In connection therewith, indicator means such as colored lamps for water and air, respectively, may be provided on the instrument carrier 3 for each instrument provided with a coolant spray device for indicating the actual control step for the water-air combination.

Thus, by means of the coolant control device 32 the composition of the coolant may be controlled individually for different instruments. In connection with the individual control, the contacts 32a and 32b in the instrument block may be connected to the coolant control device through a selector device 32c by means of which the number and order of succession of the control steps as well as the water-air combination to be associated with each step may be individually adjusted for the instrument in question.

As an example, the number of control steps may be limited to be smaller than the maximum four possible steps, and the cyclic order of succession of the steps which is run through by energization from the coolant control device may be changed, so that the control cycle for an instrument may comprise, for example, the steps no coolant, water and air, water alone, and air alone in order of succession and for another instrument the steps air alone and water and air in order of succession. The selector device 32c may, in principle, be constituted by a multi switch having a number of positions corresponding to the number of desired possibilities for different control cycles.

In this connection, the coolant control device may be constructed so as to allow individual adjustment for each instrument of a particular run of the control steps for that instrument as a starting step when putting the apparatus into operation.

The instrument blocks 20, 21 and 22 are connected with the instrument selector device 24 in the same manner as the instrument block 19 and may be energized from the energizing and control means 31, the coolant control 32 and the air blow energizing device 31a. With the construction of the instrument selector device 24 described in the foregoing, it will be recorded therein at any time which of the possible lifted instrument is selected for energization, so that a corresponding identification signal is made available for the input control unit 30.

The construction and function of the control circuit in FIG. 2 described in the foregoing may without difficulty be realized by means of conventional logic circuits constructed from separate components. In a preferred embodiment, however, the control circuit 23 comprises a microprocessor as a central control unit incorporating the functions of the instrument selector device 24, the mode switching device 25, the two input control units 30 and 36, the coolant control device 32, and the timing device 49, so that these devices do not occur physically as separate units. Such a microprocessor will be connected to the four instrument blocks 19 to 22 and the common operator unit 17, as well as the energizing and control means 31, the alarm device 35 and the function energizing devices 37 to 39 and possibly 45 in the control circuit 23.

In principle, the overall function of the control circuit will be the same by use of a microprocssor as in case of a control circuit built up of separate logic circuits and will be explained in the following by means of the flow chart in FIG. 3.

$P_1$ is a program loop, by means of which the microprocessor continuously scans the four instrument blocks 19 to 22. For each instrument block it is asked by $Q_1$ whether a lift-off signal occurs. If this is not the case, it is asked in the operation memory of the microprocessor at $Q_2$ whether lift-off signals have been detected for one or more of the other instrument blocks during the previous complete scan. If so, the program routine is stopped for the instrument in question.

If, on the contrary, it is detected by $Q_1$ that a lift-off signal occurs, it is asked in the operation memory of the microprocessor whether any other instrument block has been selected for energization. If so, a blocking of the instrument in question, in this case the instrument block 19, is established at $C_1$, and the program routine in question is stopped.

If it is detected at $Q_3$ that no other instrument has been selected, it is asked in the operation memory of the microprocessor whether the control member of the operator unit assumes its home position. Only if this is the case, the possibility is open for selection of the instrument block 19 for energization, and the apparatus is switched to the first mode of operation at $C_2$. Thereby, a program loop $P_2$ is initiated, in which it is first asked at $Q_5$ whether a voltage signal from the voltage divider 29 in FIG. 2 occurs, i.e. whether a horizontal movement in one direction or the other of the control member 18 out of the central position has been performed, If so, it is asked at $Q_6$ by use of the operation memory of the microprocessor whether the selected instrument is a motor driven drilling instrument with two directions of revolution and variable speed. If the answer is in the affirmative, the sign of the voltage signal is asked for at $Q_7$, i.e. whether the control member 18 has been moved to the side corresponding to counter-clockwise rotation of the drilling instrument in question. If so, the alarm device 35 is actuated at $C_3$. Thereafter, or if it has been detected at $Q_7$ that the control member has been moved to the right corresponding to clockwise rotation of the instrument, as well as in the case of a negative answer at $Q_6$, it is asked at $Q_8$ by use of the operation memory and timing unit of the microprocessor whether the duration of the movement of the control member has exceeded the above mentioned prescribed minimum time. If so, the instrument is energized at $C_4$ together with the accompanying coolant spray with the water-air combination adjusted by means of the coolant control device. Furthermore, a speed control dependent on the length of the movement of the control member 18 out of the central position is initiated.

If, on the contrary, it is detected at $Q_8$ that the minimum time has not been exceeded, the above mentioned air-blow is energized at $C_5$ which may serve to dry a cavity. This air blow may be continuously prolonged by repeated horizontal movements of short duration of the control member 18 in on direction or the other out of the central position.

If it is detected at $Q_5$ that no voltage signal occurs from the voltage divider 29 corresponding to no horizontal movement of the control member 18 which is, thus, assuming the central position, it is asked at $Q_9$ whether closure of the contact 28 corresponding to vertical movement of the control member 18 occurs. If so, the coolant control device 32 is actuated at $C_6$ to change the water-air combination of the coolant to the following control step in the control cyclus adjusted for the instrument in question by means of the selector device 32c in FIG. 2, and simultaneously a time measurement is initiated at $C_7$. Thereafter, it is asked at $Q_{10}$ whether closure of the contact has exceeded the minimum time, and if so, a further change to the next following control step is initiated at $C_6$, whereby the control steps are cyclically passed, as long as the contact 28 is kept closed with time intervals between the changes corresponding to the predetermined minimum time.

Also in an embodiment using a microprocessor, this device may be programmed so that a predetermined control step in the cyclus adjusted for the instrument in question is chosen as a start step when putting the apparatus into operation.

If no vertical movement of the control member 18 has been detected at $Q_9$ corresponding to the control member assuming exactly the central position, it is asked at $Q_{11}$ for a drilling instrument operating with coolant spray by means of the operation memory of the microprocessor whether a voltage signal from the voltage divider 29 of a longer duration than the prescribed minimum time has been detected in the preceeding scan cycle for this instrument. If so, an air-blow is automatically energized at $C_8$ preferably with two air-blows of different duration.

If it has been detected at $Q_2$ that no other instrument has been lifted off corresponding to all instruments 4 to 7 assuming their respective positions in the instrument carrier 3, a program loop 3 is initiated, in which the apparatus is first switched to the second mode of operation at $C_9$. Thereafter, it is asked at $Q_{12}$ in the same manner as at $Q_5$. If a horizontal movement of the control member 18 out of the central position is detected thereby, it is asked at $Q_{13}$ whether the movement is to the left. Dependent on the fact whether this in the case or not, the two separate auxiliary functions or set of auxiliary functions such as described in the foregoing are energized, so that in case of movement of the control member to the left, the function energizing device 37 in FIG. 2 is actuated, and in case of movement to the right actuation is made of both function energizing devices 37 and 38 in FIG. 2 at $C_{10}$ and $C_{11}$ respectively. If no horizontal movement of the control member is detected at $Q_{12}$, it is asked at $Q_{14}$ in the same manner as at $Q_9$, and at detection of a vertical movement of the control member 18 a third separate auxiliary function is generated at $C_{12}$ such as described in the foregoing by actuation of the function energizing device 39 in FIG. 2.

Figure 3:
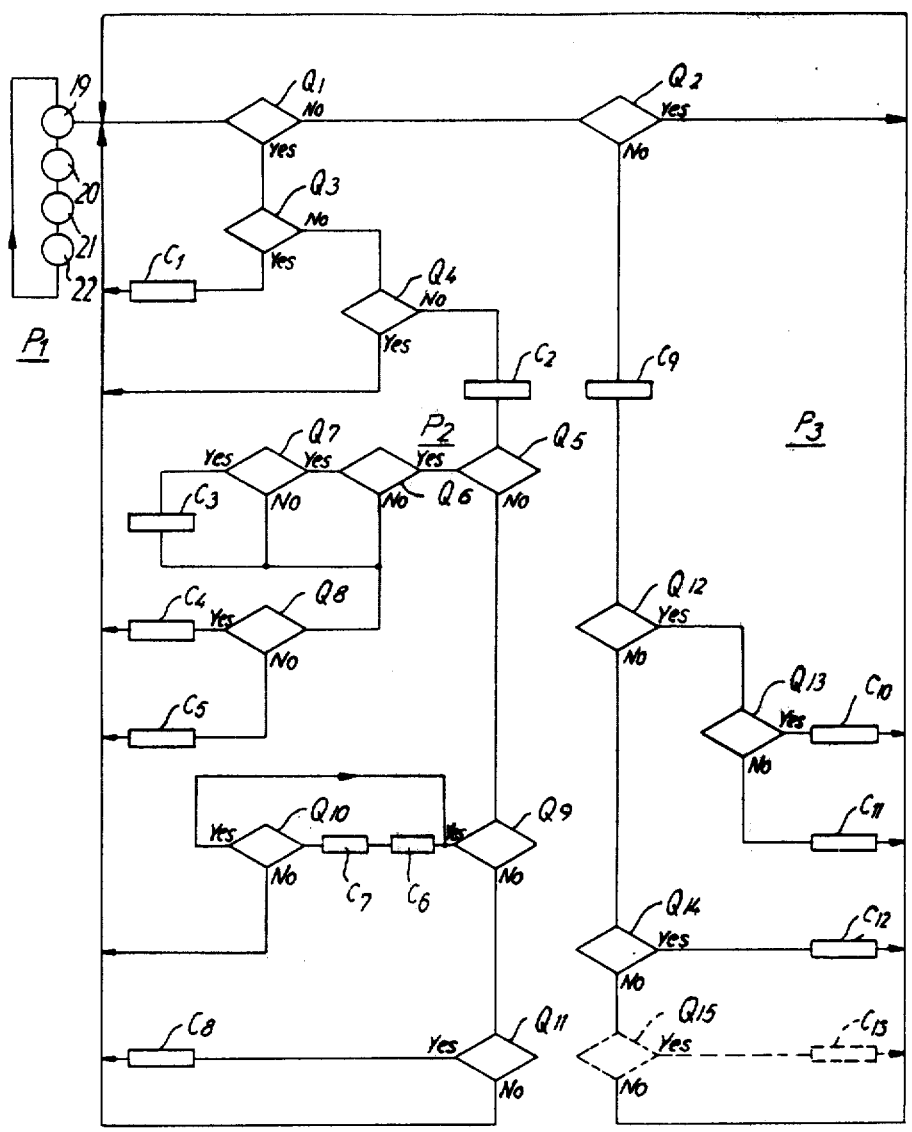
FIG. 3 is a flow chart illustrating the operation of the dental apparatus.

As shown in dashed lines in FIG. 3, the programme loop $P_3$ may be supplemented with a further loop corresponding to the above mentioned possibility of an inwards movement of the control member. If it is detected at $Q_{14}$ that no vertical movement of the control member occurs, it is asked at $Q_{15}$ whether such an inwards movement occurs and, if so, a fourth separate auxiliary function is energized at $C_{13}$ by actuation of the function energizing device 45 in FIG. 2.

Figure 4:
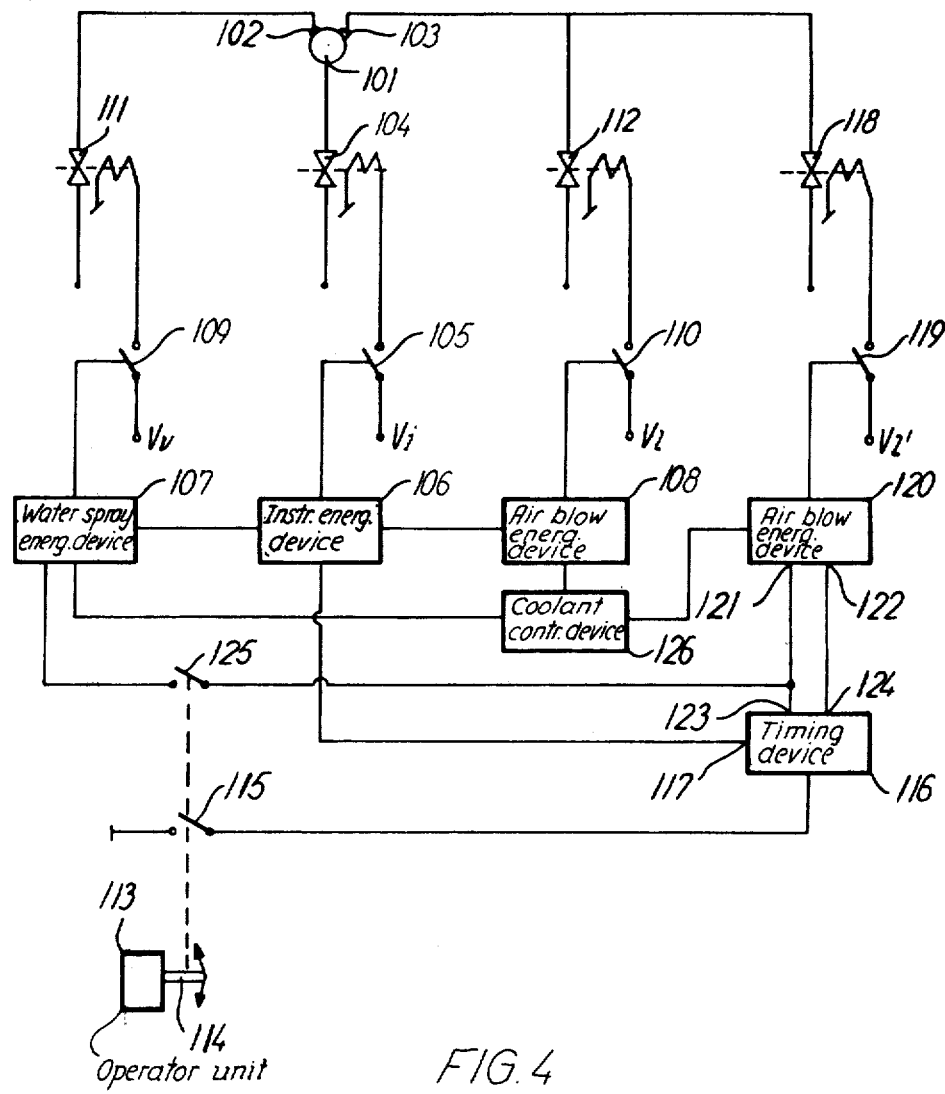
FIG. 4 shows a modification of the dental apparatus according to the invention.

FIG. 4 shows a modification of the dental apparatus particularly intended for producing an automatic air blow after each operation of a drilling instrument.

In FIG. 4, which shows only the details necessary for understanding the invention, there is attached to the shaft of a drilling instrument 101, which in the embodiment shown is powered by an air turbine, a water spraying device 102 on one hand and an air blowing device 103 on the other hand, said devices cooperating for spraying a coolant composed of water and air during operation of the drilling instrument 101.

Compressed air is supplied to the air turbine of the drilling instrument 101 by means of a magnet valve 104, which is opened by a signal $V_i$ supplied through a contact 105, which is closed by means of an energizing signal from an instrument energizing device 106. Simultaneously, this signal from the instrument energizing device 106 is supplied to a water spray energizing device 107 and an air blow energizing device 108, whereby contacts 109 and 110 are closed to supply opening signals $V_v$ and $V_1$ to magnet valves 111 and 112, respectively, which are thereby opened for the supply of water and air, respectively, to the water spraying device 102 and the air blowing device 103 to produce a coolant spray during the operation of the instrument.

In the example illustrated in which the drilling instrument 101 is controlled by an on-off control, the energizing signal from the circuit 106 is produced by means of an operator unit 113 such as a foot-contact having a control member 114, which is movable out of a home position against spring action.

The operator unit 113 may comprise, for example, a normally open contact 115, which is closed as soon as the control member 114 leaves the home position shown, whereby an input signal is supplied to a timing device 116 to which the instrument energizing device 6 is connected at an output 117.

The timing device 116 is constructed to measure the duration of the closure of the contact 115 corresponding to the movement of the control member 114 out of the home position so that only when the movement of the control member 114 exceeds a prescribed minimum time a signal is supplied at the output 117 for actuating the instrument energizing device 106.

For automatic production of a blow of pure air at the return of the control member 114 to the home position subsequent to movement out of this position, the air blowing device 103 is connected in the embodiment shown to a separate air supply having a higher pressure than used for the supply of air to the coolant by means of the magnet valve 112. This pure air blow is controlled by a separate magnet valve 118, which is activated by closure of a contact 117 controlled by a separate air blow energizing device 120 having two signal inputs 121 and 122, which are connected individually to outputs 123 and 124, respectively, of the timing device 116. However, the selective actuation of the pure air blow through the device 103 may also take place by means of the same air blow energizing device 108, which controls the supply of air through the coolant.

After return of the control member 114 to the home position a first or a second control signal is supplied from the timing device 116 to said inputs 121 and 122 of the air blow energizing device 120 in dependence on the duration of the closure of the contact 115 resulting from movement of the control member out of the home position having a shorter or longer duration than said prescribed minimum time.

In response to this signal on inputs 121 and 122 the air blow energizing device 120 generates either a first or a second opening signal for the contact 119. The first opening signal generated in response to the signal on the input 121 and caused subsequent to a short movement of the control member 114 not resulting in actuation of the instrument energizing device 106 consists preferably of a single pulse having a duration of 2 seconds, for example, whereas the second opening signal generated in response to a signal on the input 122 and caused by the return of the control member 114 to the home position subsequent to operation of the drilling instrument 101 consists preferably of at least two succeeding opening pulses of different duration such as a short pulse having a duration of 0.5 second followed by a longer pulse having a duration of 2 seconds. The air blow caused by the first short opening pulse will blow away droplets of water contained in the coolant sprayed during operation of the drilling instrument, whereas the following air blow will cause efficient drying of the cavity. The minimum duration of the movement of the control member 114 out of the home position prescribed as a condition for energization of the drilling instrument 101 may amount, for example, to 0.5 second. Thus, the above-mentioned air blow caused by a short movement of the control member 114 may be continuously extended by repeated short movement of the control member 114 within an actuation time corresponding to the duration of the above-mentioned single opening pulse.

As shown in the drawing, since the control member 114 of the operator unit 113 may be movable to both sides out of the central home position, the first control signal appearing at the output 123 of the timing device 116 as result of a short movement of the control member 114 may be utilized either for energizing pure air blow as described in the foregoing by movement of the control member 114 to one side such as to the right or for energizing a flush spray consisting of a combination of water and air. For this purpose, the water spray energizing device 107 may be connected to the above-mentioned output 123 through a contact 125, which is opened by movement of the control member 114 to said one side for energizing a pure air blow and closed by movement of the control member 114 to said other side, in this case to the left, whereas in the central position the contact 125 will be open or closed dependent on the side to which the control member 114 has been moved beforehand.

In response to the first control signal supplied at output 123 of the timing device 116 the water spray energizing device 107 generates an opening signal for the magnet valve 111 of the same duration as the above-mentioned first opening signal for the magnet valve 118.

The example shown and described represent a schematical and simplified embodiment of a dental apparatus according to the invention. Usually a dental apparatus wil comprise several instruments connected to a common control circuit and a common operator unit having a control member used for controlling all the instruments, whereby an instrument selector device influenced by removal of instruments from an instrument carrier will prevent energization of more than one instrument at a time. In this case also the air blow generated according to the invention subsequent to operation of a drilling instrument may be realized for several instruments in the same dental apparatus, such as a drilling instrument powered by an electric motor with a variable rotational speed in addition to an air turbine powered instrument.

Since such a dental apparatus may be constructed for control of the water-air combination of the coolant, the automatic air blow according to the invention may be realized so that said second opening signal is only generated after spraying of a coolant comprising water. For this purpose a coolant control device 126 may by connected to the water spray and air blow energizing devices 107 and 108 for adjusting the combination of water and air in the coolant and the air blow energizing device may be constructed to block for supply of said second opening signal to the magnet valve 118, when the coolant control device 126 is adjusted to influence the water spray energizing device 107 to block for the supply of water to the coolant.

The control of the air blow provided in accordance with the invention subsequent to operation of a drilling instrument may be realized by means of a control circuit built up in a conventional manner of separate logic components or it may be incorporated in a microprocessor control of a dental apparatus such as explained in the foregoing.

It will appear from the foregoing that a wide-extending simplification and automatization of the operation functions to be carried out by the dentist is obtained with the dental apparatus according to the invention, since auxiliary functions not related to the instrument operation are energized or carried out solely by operation of the common operator unit 17 with the control member 18.

As far as the actual auxiliary functions are concerned which are to be carried out in the second mode of operation for certain movements of the control member 18 of the operator unit 17, numerous modifications may be made within the scope of the invention relative to the examples of such functions described in the foregoing.

We claim:

1. A dental apparatus comprising an instrument carrier with a number of dental instruments arranged removably in individual positions in said carrier, instrument removal signal generators individually associated with each of said instrument positions, a control circuit common to said dental instruments, an instrument selector device incorporated in said control circuit and connected to said removal signal generators an instrument energizing and control device in said control circuit for energizing and controlling only one instrument at a time when selected by said selector device, an operator unit common to said instruments for controlling the energization and control of said selected instrument by said energizing and control device, said operator unit comprising a control member which is movable out of a home position to perform an instrument energizing movement, means in said control circuit for sensing said instrument energizing movement and actuating said energizing and control devices in response thereto, selectively actuable function energizing devices for actuating auxiliary functions during a dental treatment, which are not related to the operation of the dental instruments; at least one such functioning energizing device being incorporated in said common control circuit, a mode switching device incorporated in said common control circuit and controlled by said instrument selector device for switching the dental apparatus between first and second modes of operation in response to at least one instrument being removed from its position or all instruments assuming their respective positions in said instrument carrier, respectively, first and second input control units incorporated in said common control circuit and being connected to said operator unit by said mode switching device in said first and second mode respectively, said first input control unit being connected with said instrument energizing and control device in said first mode and said second input control unit being connected with said at least one function energizing device for energizing the auxiliary function governed by said device in response to movement of the control member of said operator unit in said second mode of operation.

2. A dental apparatus as claimed in claim 1, wherein the control member of the operator unit is disposed for planar movement in opposite directions out of said home position for operation of said dental instruments in said first mode and is further movable in said home position in at least one direction perpendicular to said planar movement, said mode switching device being constructed to transmit a number of different energizing signals to said second input control unit in said second mode of operation corresponding to the number of different directions of movement of said control member out of its home position, a number of function energizing devices corresponding to the number of different energizing signals being connected to said second input control unit for actuating individual different auxiliary functions in response to individual different ones of said energizing signals in said second mode of operation.

3. A dental apparatus comprising an instrument carrier with a number of dental instruments arranged removably in individual positions in said carrier, instrument removal signal generators individually associated with each of said instrument positions, a control circuit common to said dental instruments, an instrument selector device incorporated in said control circuit and connected to said removal signal generators, an instrument energizing and control device in said control circuit for energizing and controlling only one instrument at a time when selected by said selector device, an operator unit common to said instruments for controlling the energization and control of said selected instrument by said energizing and control means, said operator unit comprising a control member which is movable out of a home position to perform an instrument energizing movement, means in said control circuit for sensing said instrument energizing movement and actuating said energizing and control means in response thereto, selectively actuable function energizing devices for actuating auxiliary functions related to the operation of said dentral instruments, at least one such function energizing device being incorporated in said control circuit, an input control unit incorporated in said control circuit and connected with said instrument energizing and control means as well as said operator unit to sense said instrument energizing movement as well as a movement of said control member different from said instrument energizing movement, said at least one function energizing device being connected to said input control unit to be actuated therefrom in response to said different movement of the control member, a timing device connected to said input control unit for measuring the duration of said instrument energizing movement of the control member, said input control unit being constructed to actuate said instrument energizing and control means for instrument energization and control only in response to a duration of said movement exceeding a prescribed minimum duration and to actuate said function energizing device in response to a shorter duration of said movement.

4. A dental apparatus as claimed in claim 3, wherein the control member of the operator unit is movable for planar movement in opposite directions out of said home position for operation of said dental instruments and is further movable in said home position in at least one direction perpendicular to said planar movement, said operator unit being constructed to transmit a number of different energizing signals to said input control unit corresponding to the number of movement directions of the control member out of the home position, said input control unit being constructed to actuate said function energizing device in response to an energizing signal transmitted by said operator unit by said perpendicular movement of the control member.

5. A dental apparatus comprising an instrument carrier with a number of dental instruments arranged removably in individual positions in said carrier, instrument removal signal generator individually associated with each of said instrument positions, a control circuit common to said dental instruments, an instrument selector device incorporated in said control circuit and connected to said removal signal generator, an instrument energizing and control device in said control circuit for energizing and controlling only one instrument at a time when selected by said selector device, an operator unit common to said instruments for controlling the energization and control of said selected instrument by said energizing and control means, said operator unit comprising a control member which is movable out of a home position to perform an instrument energizing movement, means in said control circuit for sensing said instrument energizing movement and actuating said energizing and control means in response thereto, selectively actuable first and second function energizing devices for actuating a first and a second auxiliary function related to the operation of said dental instruments being incorporated in said control circuit, an input control unit incorporated in said control circuit and connected with said instrument energizing and control means and said first and second function energizing devices as well as said operator unit, the control member of said operator unit being disposed for planar movement in opposite directions out of said home position for operation of said dental instruments and being further movable in said home position in at least one direction perpendicular to said planar movement, said operator unit being constructed to transmit a number of different energizing signals to said input control unit corresponding to the number of movement directions of the control member out of the home position, a timing device being connected to said input control unit for measuring the duration of said planar movement of the control member, said input control unit being constructed to actuate said first function energizing device in response to the energizing signal transmited by said operator unit by said perpendicular movement of the control movement and to actuate said instrument energizing and control means and said second function energizing device in response to a duration of said planar movement of the control member exceeding or being shorter, respectively, than a prescribed minimum duration.

6. A dental unit as claimed in claim 5, wherein said timing device is constructed to measure the duration of the energizing signal also transmitted by said operator unit in response to said perpendicular movement of the control member, said first function energizing device being constructed for cyclic adjustment of its respective auxiliary function through a number of control steps, said input control unit being constructed to actuate said first function energizing device for a single step adjustment in response to a duration of the movement of said control member shorter than said prescribed minimum duration and through a number of steps in response to a longer duration of the movement of the control member.

7. A dental apparatus as claimed in claim 6, wherein at least one of said dental instruments is provided with a coolant spraying device for spraying a coolant comprising a combination of air and water during operation of the instrument, and said first function energizing device is a coolant control device for changing the combination of air and water in said coolant.

8. A dental apparatus as claimed in claim 7, wherein a selector device for individually selecting the number and order of succession of control steps for the combination of air and water in the coolant and the air-water combination of each step is connected with each instrument provided with a coolant spraying device, said coolant control device being constructed to energize a preselected control step as a start step when putting the dental apparatus into operation.

9. A dental apparatus as claimed in claim 5, wherein at least one of said dental instruments is provided with an air blowing device for producing an air blow, and said second function energizing device is an air blow energizing device.

* * * * *